United States Patent
Müller et al.

(10) Patent No.: US 6,172,094 B1
(45) Date of Patent: Jan. 9, 2001

(54) FUNGICIDE MIXTURES

(75) Inventors: Bernd Müller, Frankenthal; Hubert Sauter, Mannheim; Eberhard Ammermann, Heppenheim; Gisela Lorenz, Hambach; Siegfried Strathmann, Limburgerhof; Maria Scherer, Landau; Klaus Schelberger, Gönnheim; Joachim Leyendecker, Ladenburg, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/171,649

(22) PCT Filed: Apr. 23, 1997

(86) PCT No.: PCT/EP97/02041

§ 371 Date: Oct. 22, 1998

§ 102(e) Date: Oct. 22, 1998

(87) PCT Pub. No.: WO97/40686

PCT Pub. Date: Nov. 6, 1997

(30) Foreign Application Priority Data

Apr. 26, 1996 (DE) .............................. 196 16 716
Apr. 30, 1996 (DE) .............................. 196 17 234
Apr. 30, 1996 (DE) .............................. 196 17 231

(51) Int. Cl.[7] .......................... A01N 43/64; A01N 37/34; A01N 43/56; A01N 47/10

(52) U.S. Cl. ................... 514/383; 514/407; 514/476; 514/491; 514/528

(58) Field of Search .................. 514/407, 383, 514/476, 491, 528

(56) References Cited

U.S. PATENT DOCUMENTS

| | | | |
|---|---|---|---|
| 2,457,674 | 12/1948 | Heuberger | 167/22 |
| 2,504,404 | 4/1950 | Flenner | 167/22 |
| 3,379,610 | 4/1968 | Bruce et al. | 167/22 |
| 3,957,847 | 5/1976 | Davidson | 260/465.4 |

FOREIGN PATENT DOCUMENTS

9601256 * 1/1996 (WO) .
9601258 * 1/1996 (WO) .

OTHER PUBLICATIONS

Weeds, vol. 15, Jan. 1967, No. 1, 20–22.
Tomlin, The Pesticide Manual Incorporating The Agrochemicals Handbook, 10edition (1995), pp. 257, 258, 635–638, 689, 690 and 1048–1050.*

* cited by examiner

Primary Examiner—Allen J. Robinson
(74) Attorney, Agent, or Firm—Keil & Weinkauf

(57) ABSTRACT

A composition comprising effective amounts of
a) a carbamate of the formula I

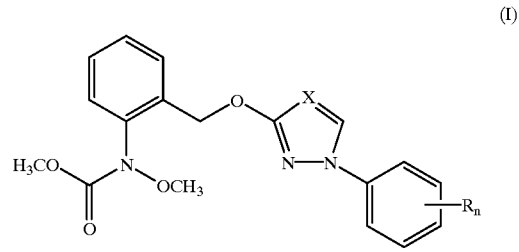

where X is CH or N, n is 0, 1 or 2 and R is halogen, $C_1$–$C_4$-alkyl or $C_1$–$C_4$-haloalkyl, it being possible for the radicals R to be different if n is 2, and
b) a dithiocarbamate (II) selected from the group consisting of
  manganese ethylenebis(dithiocarbamate) (zinc complex) (IIa),
  manganese ethylenebis(dithiocarbamate) (IIb),
  zinc ammoniate ethylenebis(dithiocarbamate) (IIc) and
  zinc ethylenebis(dithiocarbamate) (IId)
and optionally
c) 1-(2-cyano-2-methoxyiminoacetyl)-3-ethylurea (III)

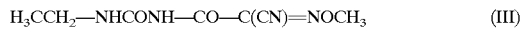

which exhibits a synergistically enhanced fungicidal effect is described.

20 Claims, No Drawings

FUNGICIDE MIXTURES

This application is a 371 of PCT/EP97/02041, filed Apr. 23, 1997.

The present invention relates to a fungicidal mixture which comprises a) a carbamate of the formula I

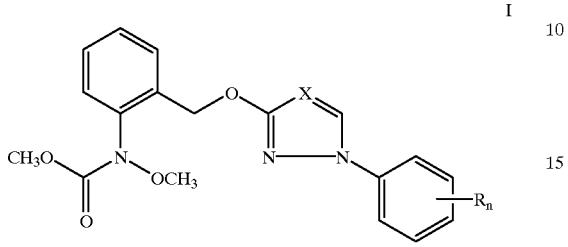

where X is CH or N, n is 0, 1 or 2 and R is halogen, $C_1$–$C_4$-alkyl or $C_1$–$C_4$-haloalkyl, it being possible for the radicals R to be different if n is 2, and b) a dithiocarbamate (II) selected from the group consisting of
manganese ethylenebis(dithiocarbamate) (zinc complex) (IIa),
manganese ethylenebis(dithiocarbamate) (IIb),
zinc ammoniate ethylenebis(dithiocarbamate) (IIc) and
zinc ethylenebis(dithiocarbamate) (IId), and/or c) 1-(2-cyano-2-methoxyiminoacetyl)-3-ethylurea (III)

$$H_3CCH_2-NHCONH-CO-C(CN)=NOCH_3 \qquad III$$

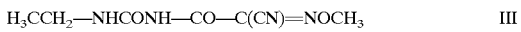

in a synergistically active amount.

Moreover, the invention relates to methods of controlling harmful fungi using mixtures of the compounds I, II and/or III and to the use of the compounds I, II and/or III for the preparation of such mixtures.

The compounds of the formula I, their preparation and their action against harmful fungi are known from the literature (WO-A 96/01,256 and WO-A 96/01,258).

Also known are the dithiocarbamates II (IIa: common name: mancozeb, U.S. Pat. No. 3,379,610; IIb: common name: maneb, U.S. Pat. No. 2,504,404; IIc: former common name: metiram, U.S. Pat. No. 3,248,400; IId: common name: zineb, U.S. Pat. No. 2,457,674), their preparation, and their action against harmful fungi.

Also known is the compound III (U.S. Pat. No. 3,957,847; common name: cymoxanil), its preparation, and its action against harmful fungi.

It is an object of the present invention to provide mixtures which have an improved action against harmful fungi combined with a reduced total amount of active ingredients applied (synergistic mixtures), with a view to reducing the rates of application and to improving the spectrum of action of the known compounds.

We have found that this object is achieved by the mixtures defined at the outset. Moreover, we have found that better control of harmful fungi is possible by applying the compound I, II and/or III simultaneously together or separately or by applying the compounds I, II and/or III in succession than when the individual compounds are used.

Mixtures of I and II or I and III and also mixtures comprising I, II and III are suitable for this purpose.

Formula I represents in particular carbamates where the combination of substituents corresponds to a line in the table below:

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Particular preference is given to the compounds I.12, I.23, I.32 and I.38.

Due to their basic character, the compounds I and III are capable of forming salts or adducts with inorganic or organic acids or with metal ions.

Examples of inorganic acids are hydrohalic acids such as hydrofluoric acid, hydrochloric acid, hydrobromic acid and hydriodic acid, sulfuric acid, phosphoric acid and nitric acid.

Suitable organic acids are, for example, formic acid, carboxylic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valences which they can assume.

When preparing the mixtures, it is preferred to employ the pure active ingredients I and II and/or III, to which further ingredients active against harmful fungi or other pests, such as insects, arachnids or nematodes, or else herbicidal or growth-regulating active ingredients or fertilizers, can be admixed, if so required.

The mixtures of the compounds I, II and/or III, or the simultaneous joint or separate use of the compounds I, II and/or III, are/is notable for outstanding action against a wide spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants, such as cotton, vegetable species (eg. cucumbers, beans and cucurbits), barley, grass, oats, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, Phytophthora infestans in potatoes and tomatoes, Pseudoperonospora species in cucurbits and hops, *Plasmopara viticola* in grapevines, Alternaria species in vegetables and fruit, and Fusarium and Verticillium species.

Furthermore, they can be used in the protection of materials (eg. in the protection of wood), for example against *Paecilomyces variotii*.

The compounds I, II and/or III can be applied simultaneously together or separately or in succession, the sequence, in the case of separate application, generally not having any effect on the result of the control measures.

The compounds I and II are usually used in a weight ratio of 200:1 to 0.1:1, preferably 100:1 to 1:1, in particular 50:1 to 5:1 (II:I).

The compounds I and III are usually used in a weight ratio of 10:1 to 0.1:1, preferably 5:1 to 0.2:1, in particular 3:1 to 1:3 (III:I).

The application rates of the mixtures according to the invention are, in the case of the compounds I, in general from 0.005 to 0.5 kg/ha, preferably 0.01 to 0.5 kg/ha, in particular 0.01 to 0.3 kg/ha, depending on the nature of the desired effect.

In the case of the compounds II, the application rates are in general from 0.1 to 10 kg/ha, preferably 0.5 to 5 kg/ha, in particular 1 to 4 kg/ha.

In the case of the compounds III, the application rates are in general from 0.005 to 0.8 kg/ha, preferably 0.01 to 0.5 kg/ha, in particular 0.05 to 0.3 kg/ha.

For seed treatment, the application rates of the mixture are generally from 0.001 to 100 g/kg of seed, preferably 0.01 to 50 g/kg, in particular 0.01 to 10 g/kg.

If phytopathogenic harmful fungi are to be controlled, the separate or joint application of the compounds I and II or III or of the mixtures of the compounds I, II and/or III is effected by spraying or dusting the seeds, the plants or the soils before or after sowing of the plants, or before or after plant emergence.

The fungicidal synergistic mixtures according to the invention, or the compounds I, II and/or III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or watering. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignosulfite waste liquors or methylcellulose.

Powders, materials for spreading and dusts can be prepared by mixing or jointly grinding the compounds I, II and/or III or the mixture of the compounds I, II and/or III with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I, II or III or of the mixture of the compounds I, II and/or III. The active ingredients are employed in a purity of from 90% to 100%, preferably 95% to 100% (according to NMR spectrum or HPLC).

The compounds I, II or III, or the mixtures, or the corresponding formulations, are applied by treating the harmful fungi or the plants, seeds, soils, areas, materials or spaces to be kept free from them with a fungicidally active amount of the mixture, or of the compounds I, II and III in the case of separate application. Application can be effected before or after infection by the harmful fungi.

Examples of the synergistic action of the mixtures according to the invention against harmful fungi.

The fungicidal action of the compound and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action, based on ethoxylated alkyl-phenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into degrees of action. The expected degrees of action of the mixtures of the active ingredients are determined using Colby's formula [R. S. Colby, Weeds 15, 20–22 (1967)] and compared with the observed degrees of action.

Colby's formula:

$$E = x + y + z - x \cdot y \cdot z / 100$$

E expected degree of action, expressed in % of the untreated control, when using the mixture of the active ingredients A, B and C at the concentrations of a, b and c x degree of action, expressed in % of the untreated control, when using active ingredient A at a concentration of a y degree of action, expressed in % of the untreated control, when using active ingredient B at a concentration of b z degree of action, expressed in % of the untreated control, when using active ingredient C at a concentration of c The efficacy (E) was calculated as follows using Abbot's formula:

$$W = (1 - \alpha) \cdot 100 / \beta$$

α corresponds to the fungal infection of the treated plants in % and

β corresponds to the fungal infection of the untreated (control) plants in %

A degree of action of 0 means that the infection level of the treated plants corresponds to that of the untreated control plants; a degree of action of 100 means that the treated plants are not infected.

EXAMPLES 1–6
Curative Action Against *Plasmopara viticola*

Leaves of potted vines of the variety "Müller-Thurgau" were inoculated with an aqueous zoospore suspension of *Plasmopara viticola*. The vines were then kept for 48 hours at 22–24° C. in a chamber saturated with water vapor. The vines were then removed from the chambers and, after drying, sprayed with an aqueous active compound preparation prepared from a stock solution of 10% of active compound, 63% of cyclohexanone and 27% of emulsifier, until dripping wet. After the spray coating had dried on, the plants were further cultivated in the greenhouse at 20–30° C. for 5 days. The plants were then kept in a chamber of high atmospheric humidity for a further 16 hours to stimulate sporulation of the fungus. The extent of the infection at the undersides of the leaves was then assessed visually.

| Ex. | Active compound | Active compound concentration in the spray liquor in ppm | Degree of action in % of the untreated control |
|---|---|---|---|
| 1V | Control (untreated) | (98% infected) | 0 |
| 2V | Compound No. 1.32 = A | 12.5 | 75 |
| 3V | Compound No. 1.38 = B | 12.5 | 70 |
| 4V | III = cymoxanil | 12.5 | 60 |

| Ex. | Active compound concentration in the spray liquor in ppm | Observed degree of action | Calculated degree of action*) |
|---|---|---|---|
| 5 | 12.5 A + 12.5 III | 100 | 90 |
| 6 | 12.5 B + 12.5 III | 100 | 88 |

*)calculated according to the Colby formula

The results of the examples show that the observed degree of action at all mixing ratios is higher than the degree of action calculated according to the Colby formula.

EXAMPLES 7–19
Action Against *Plasmopara viticola*

Leaves of potted vines of the variety "Müller-Thurgau" were sprayed with an aqueous active compound preparation prepared from a stock solution of 10% of active compound, 63% of cyclohexanone and 27% of emulsifier, until dripping wet. To be able to assess the long-term activity of the substances, the plants were kept for 7 days in the greenhouse after the spray coating had dried on. Only then were the leaves inoculated with an aqueous zoospore suspension of *Plasmopara viticola*. The vines were then kept first in a chamber saturated with water vapor at 24° C. for 48 hours, and then in a greenhouse at 20–30° C. for 5 days. The plants were then kept for a further 16 hours in a chamber of high atmospheric humidity to stimulate sporulation of the fungus. The extent of the infection at the undersides of the leaves was then determined visually.

The visually determined percentages of infected leaf area were converted into degrees of action as % of the untreated control. A degree of action of 0 is equivalent to the same extent of infection as in the untreated control, a degree of action of 100 is 0% infection. The expected degrees of action of active compound combinations were calculated according to the Colby formula (Colby, S. R. "Calculating synergistic and antagonistic responses of herbicide Combinations", Weeds, 15 (1967), 20–22) and compared with the observed degrees of action.

| Ex. | Active compound | Active compound concentration in the spray liquor in ppm | Degree of action in % of the untreated control |
|---|---|---|---|
| 7V | Control (untreated) | (90% infected) | 0 |
| 8V | Compound No. 1.32 = A | 0.63 | 90 |
|  |  | 0.31 | 60 |
| 9V | Compound No. 1.38 = B | 0.63 | 90 |
|  |  | 0.31 | 80 |
| 10V | IIb = maneb | 6.3 | 0 |

-continued

| Ex. | Active compound concentration in the spray liquor in ppm | Observed degree of action | Calculated degree of action* |
|---|---|---|---|
| 11V | IIc = metiram 3.1 | 6.3 | 0 |
| | | 3.1 | 0 |
| | | | 0 |
| 12 | 0.63 A + 6.3 IIb | 98 | 90 |
| 13 | 0.31 A + 3.1 IIb | 93 | 60 |
| 14 | 0.63 A + 6.3 IIc | 100 | 90 |
| 15 | 0.31 A + 3.1 IIc | 75 | 60 |
| 16 | 0.63 B + 6.3 IIb | 98 | 90 |
| 17 | 0.31 B + 3.1 IIb | 97 | 80 |
| 18 | 0.63 B + 6.3 IIc | 98 | 90 |
| 19 | 0.31 B + 3.1 IIc | 95 | 80 |

*)calculated according to the Colby formula

The results of the tests show that the observed degree of action at all mixing ratios is higher than the degree of action calculated according to the Colby formula.

We claim:

1. A fungicidal composition comprising synergistically effective amounts of
   a) a carbamate I

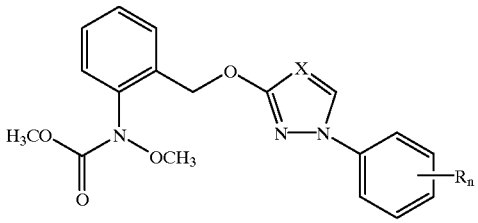

(I)

where X is CH or N, n is 0, 1 or 2 and R is halogen, $C_1$–$C_4$-alkyl or $C_1$–$C_4$-haloalkyl, it being possible for the radicals R to be different if n is 2, and
   b) a dithiocarbamate (II) selected from the group consisting of
      manganese ethylenebis(dithiocarbamate) (zinc complex) (IIa),
      manganese ethylenebis(dithiocarbamate) (IIb),
      zinc ammoniate ethylenebis(dithiocarbamate) (IIc) and
      zinc ethylenebis(dithiocarbamate) (IId).

2. The composition defined in claim 1, wherein the dithiocarbamate (II) is manganese ethylenebis (dithiocarbamate) (zinc complex) (IIa).

3. The composition defined in claim 1, wherein the dithiocarbamate (II) is manganese ethylenebis (dithiocarbamate) (IIb).

4. The composition defined in claim 1, wherein the dithiocarbamate (II) is zinc ammoniate ethylenebis (dithiocarbamate) (IIc).

5. The composition defined in claim 1, wherein the dithiocarbamate (II) is zinc ethylenebis(dithiocarbamate) (IId).

6. The composition defined in claim 1, wherein the weight ratio of the dithiocarbamate II to the carbamate I is 200:1 to 0.1:1.

7. The fungicidal composition defined in claim 1, further comprising 1-(2-cyano-2-methoxyiminoacetyl)-3-ethylurea (III).

8. The fungicidal composition defined in claim 7, wherein the dithiocarbamate (II) is manganese ethylenebis (dithiocarbamate) (zinc complex) (IIa).

9. The fungicidal composition defined in claim 7, wherein the dithiocarbamate (II) is manganese ethylenebis (dithiocarbamate) (IIb).

10. The fungicidal composition defined in claim 7, wherein the dithiocarbamate (II) is zinc ammoniate ethylenebis(dithiocarbamate) (IIc).

11. The fungicidal composition defined in claim 7, wherein the dithiocarbamate (II) is zinc ethylenebis (dithiocarbamate) (IId).

12. The fungicidal composition defined in claim 7, wherein the weight ratio of the dithiocarbamate (II) to the carbamate I is from 200:1 to 0.1:1.

13. The fungicidal composition defined in claim 7, wherein the weight ratio of 1-(2-cyano-2-methoxyiminoacetyl)-3-ethylurea to the carbamate I is from 10:1 to 0.1:1.

14. A method of controlling harmful fungi, which comprises treating the harmful fungi, their environment, or the plants, seeds, soils, areas, materials or spaces to be kept free from said fungi with synergistically effective amounts of a carbamate I and a dithiocarbamate II as set forth in claim 1.

15. The method defined in claim 14, wherein the carbamate I is applied in an amount of from 0.005 to 0.5 kg/ha.

16. The method defined in claim 14, wherein the dithiocarbamate (II) is applied in an amount of from 0.1 to 10 kg/ha.

17. The method defined in claim 14, further comprising treating the harmful fungi, their environment, or the plants, seeds, soils, areas, materials or spaces to be kept free from said fungi with a synergistically effective amount of 1-(2-cyano-2-methoxyiminoacetyl)-3-ethylurea.

18. The method defined in claim 17, wherein the carbamate I is applied in an amount of from 0.005 to 0.5 kg/ha.

19. The method defined in claim 17, wherein the dithiocarbamate (II) is applied in an amount of from 0.1 to 10 kg/ha.

20. The method defined in claim 17, wherein 1-(2-cyano-2-methoxyiminoacetyl)-3-ethylurea is applied in an amount of from 0.005 to 0.8 kg/ha.

* * * * *